United States Patent [19]
Ruschke

[11] Patent Number: 6,063,109
[45] Date of Patent: May 16, 2000

[54] DEVICE FOR THE COHERENT AMPLIFICATION OF ELECTROMAGNETIC OSCILLATIONS

[76] Inventor: Thomas Ruschke, Willy-Brandt-Strasse 3, 24340 Eckernfoerde, Germany

[21] Appl. No.: 09/154,634

[22] Filed: Sep. 17, 1998

[30] Foreign Application Priority Data

Sep. 25, 1997 [DE] Germany ............................ 197 42 299

[51] Int. Cl.⁷ ................................................ A61B 17/36
[52] U.S. Cl. .................................. 607/89; 606/16; 606/17
[58] Field of Search ..................... 606/1, 14, 15, 606/16, 17, 10, 12; 607/89, 90

[56] References Cited

U.S. PATENT DOCUMENTS

| | | | |
|---|---|---|---|
| 5,209,748 | 5/1993 | Daikuzono | 606/15 |
| 5,219,346 | 6/1993 | Wagnieres et al. | 606/17 |
| 5,269,777 | 12/1993 | Doiron et al. | 606/15 |
| 5,415,655 | 5/1995 | Fuller et al. | 606/17 |
| 5,445,146 | 8/1995 | Bellinger . | |
| 5,536,265 | 7/1996 | van den Bergh et al. | 606/16 |
| 5,738,681 | 4/1998 | Shimiza | 606/17 |
| 5,762,493 | 6/1998 | Rechmann | 606/16 |

FOREIGN PATENT DOCUMENTS

| | | |
|---|---|---|
| 0 184 928 | 6/1986 | European Pat. Off. . |
| 87 17 812 | 5/1990 | Germany . |
| 90 12 470 | 1/1991 | Germany . |
| 42 12 393 | 12/1992 | Germany . |
| 295 10 124 | 9/1996 | Germany . |
| 296 13 183 | 11/1996 | Germany . |

*Primary Examiner*—Linda C. M. Dvorak
*Assistant Examiner*—Sonya Harris Ogugua
*Attorney, Agent, or Firm*—Pillsbury Madison & Sutro

[57] ABSTRACT

A system composed of a device 4 for the coherent amplification of electromagnetic oscillations by means of induced emission through a solid element, crystals or glasses doped with neodymium, semiconductor diodes or liquids or gases, whereby the electromagnetic oscillations emerging from the device are conducted through a cable or optical fiber cable 2 in order to influence a biological system, especially a human body or an animal body 11. The cable 2 has an outlet opening 7 and the oscillations emerging from the cable 2 are conducted through a solid element, a mixture or a liquid or gaseous solution 8 in order to influence the biological system 11, whereby the solid element, the mixture or the liquid or gaseous solutions contain mineral, plant, animal or human extracts or products or else toxins as admixtures.

16 Claims, 2 Drawing Sheets

DEVICE FOR THE COHERENT AMPLIFICATION OF ELECTROMAGNETIC OSCILLATIONS

BACKGROUND OF THE INVENTION

The invention relates to a device for the coherent amplification of electromagnetic oscillations by means of induced emission through a solid element, crystals or glasses doped with neodymium, semiconductor diodes or liquids or gases, whereby the electromagnetic oscillations emerging from the device are conducted through a cable or optical fiber cable in order to influence a biological system, especially a human body or an animal body.

Devices are already known which are used in the field of medicine for the coherent amplification of electromagnetic oscillations by means of induced emission through a solid element. With the known lasers, there is an interest in high pulsed power and bundling of the laser beams. Currently, only detachment of the retina and certain types of brain cancer are treated with laser beams. The treatment of detachment of the retina is simple and the patient does not have to be anesthetized. After the surgeries that have been performed so far, patients who have been operated on do not feel any pain, and they only perceive a glare for some time, which is due to the effect of the laser light and to chemical processes on the retina or in the optic nerve. As far as treatment of cancer in the brain with laser beams is concerned, the selected site is struck by the laser beam, causing vaporization of the tissue.

BRIEF SUMMARY OF THE INVENTION

In contrast to this, the invention is based on the objective of improving the device for the coherent amplification of electromagnetic oscillations by means of induced emission as compared to the prior art laser devices and of exerting a positive influence on a biological system and/or of considerably accelerating the curative treatment, for example, the healing of wounds, burns, broken bones, tumors, contusions or bruises.

The objective is achieved according to the invention in that the cable has an outlet opening and the oscillations or beams emerging from the cable are conducted through a solid element, a mixture or a liquid or gaseous solution in order to influence the biological system, whereby the solid element, the mixture or the liquid or gaseous solutions contain mineral, plant, animal or human extracts or products or else toxins as admixtures.

In contrast to the technical or thermal effect that has been associated with the use of laser technology until now such as, for example, pulverizing, cutting, welding or vaporizing, the device according to the invention and the interaction between the admixtures and the electromagnetic beams in the visible range have brought specific effects to the fore, and as a result, these admixtures can be used in a curative manner. An effective healing is achieved within a short time in an optimal manner through the interaction between the light beams and the substances contained in the solid elements or mixtures. By means of the laser beam, the biological system receives the necessary energy in conjunction with the substance-specific information while utilizing the Ramann effect. In the case at hand, for example, a wound was first cared for in the classical medical manner and treated with antibiotic bandages. At the beginning of the treatment, the wound had a length of 18 cm and a width of 2.5 cm in the middle. Raw flesh could be seen in the wound. The laser irradiation, in conjunction with the substance incorporated into the laser beam in a concentration of 100 vol.-% to $10 \times 10^{-24}$ vol.-%, was able to effectuate optimal healing within an extremely short period of time, i.e., in three weeks. This is also achieved in an advantageous manner in that, through the emerging light, the laser beam conducted through the substance receives information that optically corresponds to the fingerprint of the incorporated substance. In any case, the emerging laser beam is conducted through the solid element or the liquid or gaseous solution with the admixture that functions as the optical device and said beam is directed at the wound. The treatment of a wound having a surface area of 25 cm$^2$ can take 30 minutes. Such a treatment over the course of a week on a daily basis brings about an intense healing reaction, whereby the wound size finally shrinks to 4 cm$^2$ and has a circular scab after about two weeks. If such a treatment process is continued over a period of three weeks, a wound having a surface area of 25 cm$^2$ can heal completely.

For this purpose, it is advantageous for the cable to have an inlet opening as well as the outlet opening, whereby the outlet opening opens up into the inlet opening of a treatment probe and the solid element, the mixture or the gaseous or liquid solution is provided or can be placed between the inlet and outlet openings.

An additional possibility according to another embodiment of the device of the invention is for the treatment probe or the receptacle to have a longitudinal opening and, intersecting the longitudinal opening at an angle, to have a crosswise opening into which the solid element, the mixture or the gaseous or liquid solution can be placed directly or indirectly.

In another embodiment of the invention, it is advantageous for the crosswise opening to lie in the beam path of the electromagnetic oscillations or of the laser beam and to serve to hold a container that serves to receive the solid element, the mixture or the gaseous or liquid solution.

Finally, a preferred embodiment of the solution according to the invention provides that the container to receive the solid element, the gaseous or liquid substance or the mixture is made of glass or quartz glass.

It is of special importance for the present invention that the container can be placed into the crosswise opening and can be clamped and/or secured there.

In conjunction with the configuration and arrangement, it is advantageous for the container to be provided with a closure mechanism.

Moreover, it is advantageous for the device or the laser device to be designed as an argon-ion laser and/or as an argon-ion multi-line laser for frequencies ranging from $5 \times 10^{14}$ Hz to $5 \times 10^{15}$ Hz.

Furthermore, it is advantageous for the admixture placed into the container to be added to a carrier solution consisting of water and ethanol, whereby the admixture of the substances is present in a concentration of 90 vol.-% to $10 \times 10^{-24}$ vol.-%.

For this purpose, it is advantageous for the laser device to have a power output between 30 mW and 100 mW or 40 mW and 70 mW or 45 mW and 65 mW or 45 mW and 55 mW, especially 50 mW. If very large body areas are being treated, the power can be increased in accordance with the surface area.

Moreover, it is advantageous for the laser to be designed as an argon-ion-krypton mixed-gas laser.

Another possibility according to an embodiment of the device according to the invention is for the laser to be designed as an He—Ne laser.

In another embodiment of the invention, it is advantageous for the laser to be designed as an He—Cd laser.

Moreover, it is advantageous for the laser to be designed as a multi-line/single-line, multi-mode or variable-frequency laser.

In another embodiment of the invention, it is advantageous for the laser to be designed as a diode laser for frequencies from $5 \times 10^{14}$ Hz to $10^{15}$ Hz.

An additional possibility according to another embodiment of the device of the invention is for the laser to be designed as a crystal laser or as a neodymium-yag laser.

It is also advantageous that a solid element or a gaseous or liquid mixture that is present in a concentration of $10 \times 10^{-3}$ vol.-% to $10 \times 10^{-9}$ vol.-% can placed into the receptacle for the treatment of contusions.

An essential advantageous embodiment is achieved in that a solid element or a gaseous or liquid mixture that is present in a concentration of $10 \times 10^{-3}$ vol.-% to $10 \times 10^{-12}$ vol.-% can be placed into the receptacle for the treatment of broken bones, whereby the argon-ion laser device is used for this purpose.

Moreover, it is advantageous that a solid element or a gaseous or liquid mixture that is present in a concentration of $10 \times 10^{-6}$ vol.-% to $10 \times 10^{-8}$ vol.-% can be placed into the receptacle for the treatment of tumors, whereby the argon-krypton mixed-gas laser device is used for this purpose.

Furthermore, it is advantageous that a solid element or a gaseous or liquid mixture that is present in a concentration of $10 \times 10^{-3}$ vol.-% to $10 \times 10^{-9}$ vol.-% can be placed into the receptacle for the treatment of concussions, whereby the argon-ion laser device is used for this purpose.

An additional possibility is that a solid element or a gaseous or liquid mixture that is present in a concentration of $10 \times 10^{-1}$ vol.-% to $10 \times 10^{-24}$ vol.-% can be placed into the receptacle for the treatment of metabolic disorders, whereby the argon-ion and/or argon-krypton mixed-gas and/or diode and/or neodymium-yag and/or He—Ne and/or He—Cd laser device is used for this purpose.

An arrangement for carrying out the process according to the invention is that a solid element or a gaseous or liquid mixture that is present in a concentration of 100 vol.-% to $10 \times 10^{-24}$ vol.-% can be placed into the receptacle for the treatment of cell cultures, whereby the argon-ion, argon-krypton, krypton, diode, neodymium-yag, He—Ne, or He—Cd laser device is used for this purpose.

The concentrations given in this description are homogeneous mixtures of various substances. For practical purposes, the concentration of a given substance is preferably expressed in percent by weight or by volume (weight or volume proportion x 100 vol.-%). For theoretical considerations, the mol fraction (mols per sum of the mols), the molarity (mols per liter of solution) or the molality (mols per kg of solvent) constitute a suitable measure of concentration.

Further advantages and details of the invention will explained below with reference to the drawing.

DETAILED DESCRIPTION OF THE INVENTION

Figure 1:
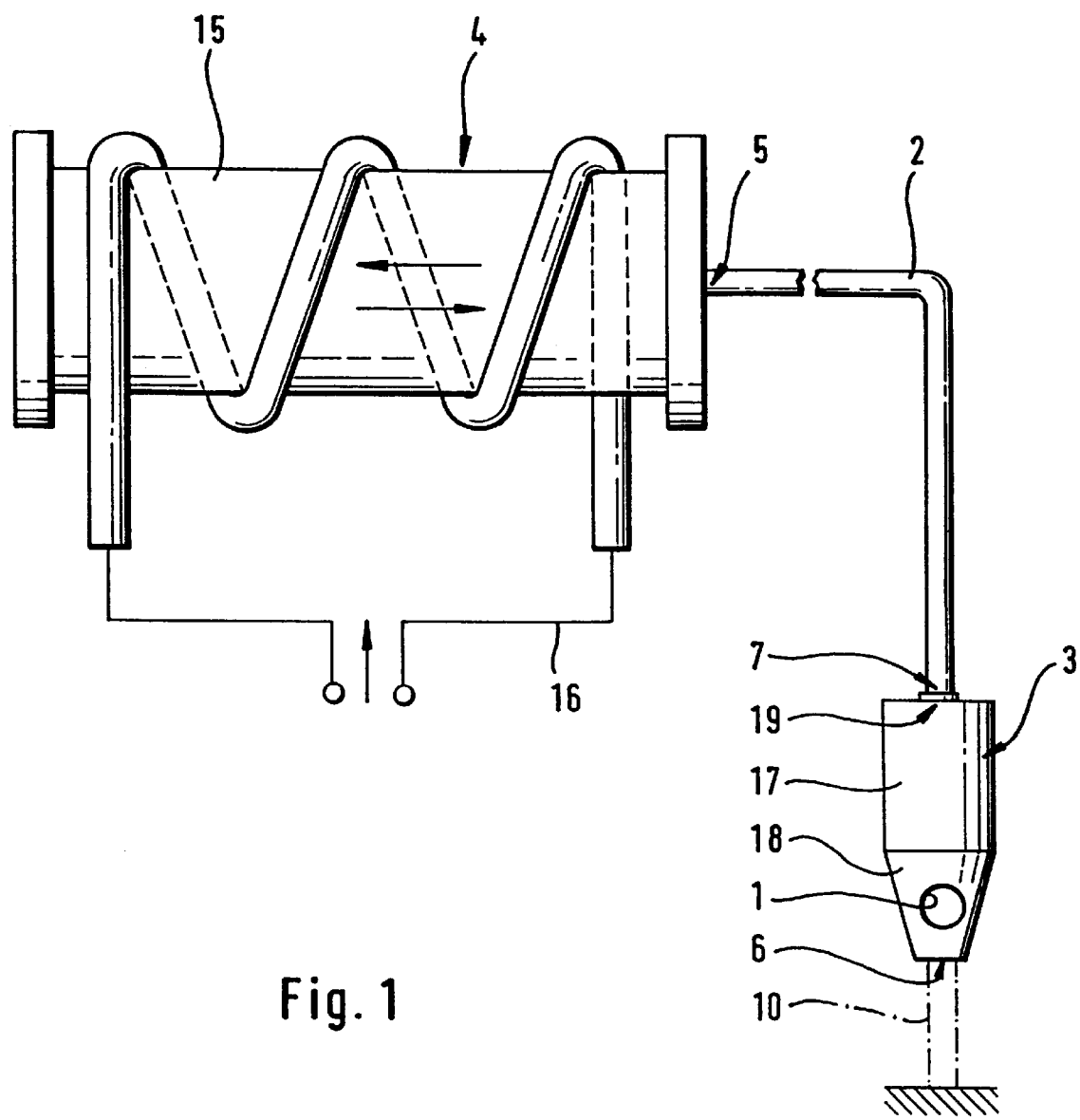
FIG. 1 is an elevational view of a laser device according to the invention with a cable or optical fiber cable provided at the outlet opening of the laser device.

In FIG. 1 of the drawing, a device for the coherent amplification of electromagnetic oscillations is designated with the numeral 4. The device 4 consists of a laser tube 15 containing an argon-ion gas, for example, for burns. Energy is transmitted to the laser device 4 through an electric line 16. The electromagnetic oscillations, waves or the laser beam emerging from the laser device 4 can have frequencies of $5 \times 10^{14}$ Hz to $10^{15}$ Hz (visible range). Depending on the curative treatment or type of application, the laser device can be designed in such a way that it can be used in the ultraviolet or infrared range. The frequencies given here constitute the visible part (light) of the electromagnetic spectrum.

A laser beam or a light beam 10 is conducted through a cable 2 whose inlet opening 5 is connected to the laser device 4 and to its outlet opening, and to an inlet opening 19 of a treatment probe or receptacle 3. The laser beam 10 emerges to the outside via the outlet opening 6 and is directed at a biological system 11.

The receptacle 3 consists of a cylindrical housing part 17 with an adjacent housing part 18 that is tapered towards the front. Over the entire length of the receptacle 3, there is a longitudinal opening 9 that opens up into the outlet opening 6. Thus, the light or laser beam 10 is conducted via the longitudinal opening 9, said light or laser beam is then conducted via the outlet opening 6 provided in the receptacle, it strikes the biological system 11 or a human body, an animal body or a plant body, where it brings about the desired healing effect or change in the biological system. In the range of the outlet opening 6 of the receptacle 3, there is a crosswise opening 1 that intersects the longitudinal opening 9 at an angle, advantageously at a right angle.

Figure 2:
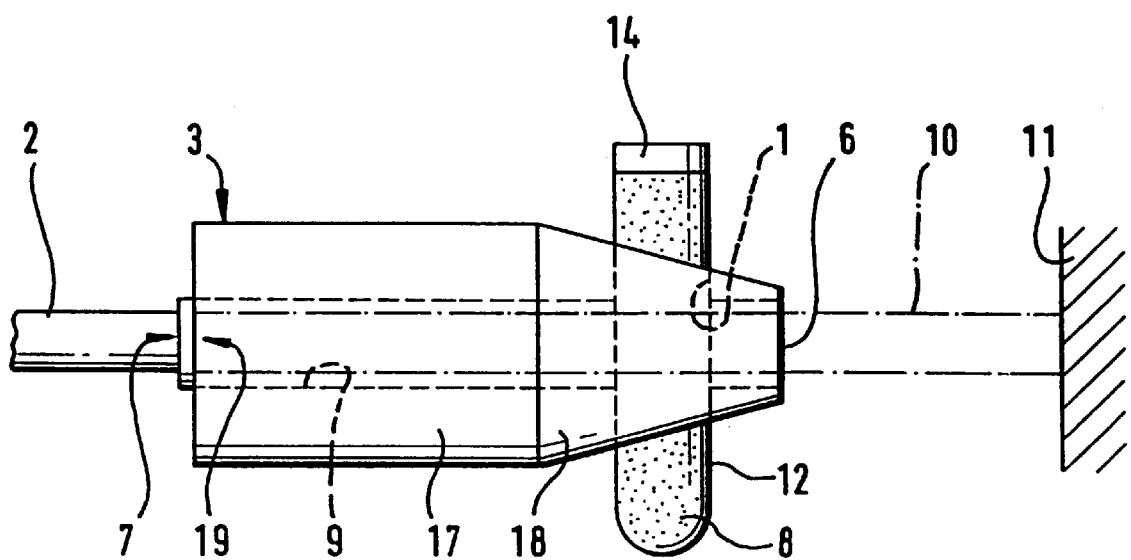
FIG. 2 is an elevational view of a treatment probe or a receptacle constituting a component of the device of FIG. 1.

As can be seen in FIG. 2, a container 12 is inserted into the crosswise opening 1 in such a way that it intersects the beams of the laser beam at an angle of 90°. As a result, the laser beams are conducted via or through the container 12. The container 12 is advantageously made of glass, especially of quartz glass, so that almost no losses occur when the laser beam passes through the quartz glass. The container may be closed by a removable closure mechanism 14, such as a lid or stopper.

Therefore, the container 12 can advantageously be cylindrical in shape. However, it is also possible to configure the container 12 so as to be conical and to adapt the corresponding crosswise opening 1 likewise to the conical shape of the container 12 so that a clamp connection between the receptacle 3 and the container 12 is achieved.

The container 12 serves to receive one or more solid elements or else to receive substances in pulverulent form or to receive a gaseous or liquid solution. In addition, a carrier solution, for example, water and ethanol at a ratio of 1:1, can be filled into the container 12. The admixtures or substances are placed into the carrier solution in a concentration of 50 vol.-% to $10 \times 10^{-24}$ vol.-% in a decreasing direction. Additionally, for example, mineral, plant, animal or human extracts or products or else toxins are added to this carrier solution. These additives are referred to as admixture 8, which is decisive for exerting a positive influence on the biological system 11 or for the medical treatment in question.

Thus, the filling of the container 12 can be a true solution, a solution mixture or a colloidal solution. Depending on the composition of the admixture, it is also possible to do without the carrier solution.

The laser beam 10 is conducted through the container 12 with the substances or admixtures and then strikes the biological system 11. In an advantageous manner, the light radiation is specifically scattered (utilization of the Ramann effect) in every atomic or molecular compound, and the emerging light practically contains the fingerprint of the admixtures. If, for example, an argon-ion laser is used, this laser beam provides the appropriate basic energy for the biological processes. The emerging laser beam then passes on the information to the biological system and brings about the healing process, for example, in the case of a burn.

The distance between the outlet end of the receptacle 3 and the biological system 11 is usually constant during the treatment process. If the distance between the outlet end of the receptacle 3 and the biological system 11 is increased, then a larger surface area of the biological system is also reached by the laser beam 10.

If a neodymium-yag laser is used, for instance, for treating wounds or for another type of treatment, it is advantageous if the wavelength of 532 nm (green) and 473 nm (blue) are used.

It is especially advantageous for the laser emission to lie in the visible range, that is to say, between 650 nm and 300 nm (UV). The selection of the wavelength depends on which biological system 11 is to be irradiated. Infrared light should not be used for human cells since it can kill them.

If the laser device is used, for example, for tumor treatment, then the laser consists of an argon-ion-krypton mixed-gas laser between 2 mm and 100 mm.

In this case, the following admixtures are placed into the container:

a) Local: extracts from pathogens of tuberculosis and/or gonorrhea and/or syphilis in a concentration of $10 \times 10^{-6}$ vol.-% to $10 \times 10^{-8}$ vol.-%.

b) Limbic system (brain): extract from Salamandra $10 \times 10^{-6}$ vol.-% to $10 \times 10^{-8}$ vol.-%.

For the treatment of broken bones, it is advantageous to use an argon-ion laser device between 2 mm and 100 mm.

For this treatment, substances of the type listed below are used as admixtures. The explanations given above show that a very specific type of laser with a corresponding probe has to be used for the medical treatment of the biological system 11, depending on the type of illness, whereby a certain admixture 8 is incorporated into each probe or receptacle.

A patient born in 1927 was found to have an open wound on the left thigh that would not heal. This wound could not be positively influenced by any of the classical treatments (e.g., administration of antibiotics, surgical treatment of the edge of the wound). This wound was treated with the described argon-ion laser, whereby the frequencies emitted were in the visible range. The power output of the laser device 4 was 50 mW. The laser beam 10 was directed at the burn 11 through the substances 8 present in the quartz glass container 12. Several substances were contained in the carrier solution in the following concentration: extract from Aconitum $10 \times 10^{-4}$ vol.-% and extract from Arnica $10 \times 10^{-3}$ vol.-%.

The emerging laser beam 10, as already mentioned, was radiated over the entire wound through the container 12 that functioned as an optical device. The treatment duration was 30 minutes each time. Already after a week, an intense healing reaction set in. After one week of treatment, the wound that had been 10 cm long and 2.5 cm wide in the middle at the beginning of the laser treatment was 2 cm in diameter after one week and 7 mm in diameter after two weeks. After three weeks, the wound had healed completely.

The laser radiation was used successfully for treating wounds, broken bones, sprains, compressions and concussions.

Following a severe concussion and laser treatment applied within five minutes, the patient was already completely free of symptoms after a ten-minute treatment, and a normal neurological reaction was observed.

Depending on the type of treatment, the appropriate laser with the appertaining container 12 containing an appropriate admixture is used.

The laser treatment or irradiation can also exert a positive influence on the metabolism. The appropriate admixtures contain extracts from plants, from animal and human products, also extracts from viruses, bacteria, fungi and other pathogens as well as extracts from tumors and pathological secretions.

Cell cultures and living cells can be positively influenced in the case of organ donation. Moreover, it is advantageous to use the laser radiation for microorganisms and also viruses outside of living organisms.

The following solutions have been successfully used for wound treatment in the following concentrations:

| | |
|---|---|
| Extract from Aconitum | $10 \times 10^{-4}$ vol.-% |
| Extract from Arnica | $10 \times 10^{-3}$ vol.-% |
| Extract from Belladonna | $10 \times 10^{-4}$ vol.-% |
| Extract from Bellis | $10 \times 10^{-4}$ vol.-% |
| Extract from Calendula | $10 \times 10^{-5}$ vol.-% |
| Extract from Chamomilla | $10 \times 10^{-4}$ vol.-% |
| Extract from Echinacea ang. | $10 \times 10^{-4}$ vol.-% |
| Extract from Echinacea purp. | $10 \times 10^{-4}$ vol.-% |
| Extract from Hamamelis | $10 \times 10^{-3}$ vol.-% |
| Extract from Millefolium | $10 \times 10^{-4}$ vol.-% |
| Extract from Symphytum | $10 \times 10^{-9}$ vol.-% |
| Solution of Hepar sulf. | $10 \times 10^{-9}$ vol.-% |
| Solution of Mercurius sol. | $10 \times 10^{-9}$ vol.-% |
| Solution of Quartz | $10 \times 10^{-6}$ vol.-% |

These and other concentrations are placed into the container 12. The container 12 functions as an optical element or as a lens and amplifies the laser beam 10. When the laser beam strikes an atom or molecule, the laser beam is scattered, i.e., the above-mentioned Ramann effect is utilized. The emerging laser beam contains the above-mentioned optical fingerprint of the substances listed above and has an influence on the treatment of the biological system 11. The scattered beams produce a bio-photon field.

Argon-ion lasers are used to treat broken bones, and substances 8 are placed into the container 12. This admixture or substance has a concentration of $10 \times 10^{-3}$ vol.-% to $10 \times 10^{-12}$ vol.-%.

A red diode laser 632 nm is used for the treatment of wild roses and a mixed quartz is added in the concentration of $10 \times 10^{-6}$. (When wild roses are treated with a laser, germs or fungi can be controlled, and wild roses can be grafted better after a laser treatment. This underscores the fact that a laser treatment can easily be carried out in plants.)

If, for example, the laser device is used for allergy treatment, then the laser consists of a red He—Ne or diode laser at 632 nm and a green He—Ne/neodymium-yag laser.

In this case, the following admixtures are placed into the container: extract from *Dioscorea vilosa* in the concentration of $10 \times 10^{-5}$ vol.-% and Kalium carb. in the concentration of $10 \times 10^{-6}$ vol.-%.

For treating hair loss, the laser consists of a green He—Ne or neodymium-yag laser.

In this case, the following admixtures are placed into the container: extract from tuberculosis and/or placenta and/or extract from *Pel talpae* in the concentration of $10 \times 10^{-3}$ vol.-% to $10 \times 10^{-9}$ vol.-%.

If the laser device is used for treating enteritis, then the laser consists of a green He—Ne or neodymium-yag laser alternating with a yellow He—Ne laser.

In this case, the following admixtures are placed into the container: extracts from pathogens in the concentration of $10\times10^{-4}$ to $10\times10^{-12}$ vol.-%.

If the laser is used, for example, for the treatment of circulatory disorders, then the laser consists of a red He—Ne diode laser.

In this case, the following admixtures are placed into the container: extracts from pathogens and/or snake venom in the concentration of $10\times10^{-4}$ vol.-% to $10\times10^{-12}$ vol.-%.

In order to treat eczema, the laser consists of a green laser alternating with an argon-ion multi-line laser.

In this case, the following admixtures are placed into the container: extracts from pathogens in the concentration of $10\times10^{-4}$ to $10\times10^{-12}$ vol.-%.

For the treatment of lowered resistance (weakened immune system), the laser consists of a red He—Ne diode laser.

In this case, the following admixtures are placed into the container: extracts from pathogens in the concentration of $10\times10^{-4}$ to $10\times10^{-12}$ vol.-%.

In order to treat hepatic colic, the laser consists of a green He—Ne or neodymium-yag laser.

In this case, the following admixtures are placed into the container: extracts from pathogens, magnesium phosphate and calcium phosphate in the concentration of $10\times10^{-4}$ Vol.-% to $10\times10^{-12}$ vol.-%.

If the laser is used, for example, for the treatment of stomach ailments, then the laser consists of a red He—Ne diode laser.

In this case, the following admixtures are placed into the container: extracts from pathogens in the concentration of $10\times10^{-4}$ to $10\times10^{-12}$ vol.-%.

If the laser device is used to treat joint disorders, then the laser consists of an argon-ion multi-line laser.

In this case, the following admixtures are placed into the container: extracts from pathogens in the concentration of $10\times10^{-4}$ to $10\times10^{-12}$ vol.-%.

For the treatment of digestive organs and the kidneys, the laser consists of a yellow and a green He—Ne laser.

In this case, the following admixtures are placed into the container: extracts from pathogens in the concentration of $10\times10^{-4}$ to $10\times10^{-12}$ vol.-% and/or minerals in the concentration of $10\times10^{-3}$ vol.-% to $10\times10^{-24}$ vol.-% and/or extract from Salamandra in the concentration of $10\times10^{-8}$ vol.-%.

If the laser is used for the treatment of Herpes and Herpes zoster, then the laser consists of an argon-ion multi-line laser.

In this case, the following admixtures are placed into the container: extract from tuberculosis in the concentration of $10\times10^{-6}$ vol.-%.

For the treatment of neuritis (ischialgia), the laser consists of an argon-ion multi-line laser.

In this case, the following admixtures are placed into the container: extract from tuberculosis in the concentration of $10\times10^{-6}$ vol.-%.

In order to treat cardiac insufficiency, anginal disorders, the laser consists of an orange He—Ne laser.

In this case, the following admixtures are placed into the container: extracts from pathogens in the concentration of $10\times10^{-4}$ to $10\times10^{-12}$ vol.-% and/or minerals in the concentration of $10\times10^{-3}$ to $10\times10^{-24}$ vol.-% and/or extract from Salamandra in the concentration of $10\times10^{-8}$ vol.-%.

If the laser device is used, for example, to treat migraine, then the laser consists of an argon-ion multi-line laser and a red He—Ne diode laser.

In this case, the following admixtures are placed into the container: extract from tuberculosis in the concentration of $10\times10^{-6}$ vol.-%.

In order to treat neurodermatitis, the laser consists of an argon-krypton mixed gas laser and a red He—Ne diode laser.

In this case, the following admixtures are placed into the container: extracts from pathogens in the concentration of $10\times10^{-4}$ to $10\times10^{-12}$ vol.-% and/or minerals in the concentration of $10\times10^{-3}$ to $10\times10^{-24}$ vol.-% and/or extract from Salamandra in the concentration of $10\times10^{-8}$ vol.-% and an extract from *Dioscorea vilosa* in the concentration of $10\times10^{-5}$ vol.-% and Kalium carb. in the concentration of $10\times10^{-6}$ vol.-%.

If the laser is used to treat Parkinson's disease, then the laser consists of argon-ion multi-line laser and an argon-krypton mixed-gas laser.

In this case, the following admixtures are placed into the container: extracts from pathogens in the concentration of $10\times10^{-4}$ to $10\times10^{-12}$ vol.-% and extracts from hormones in the concentration of $10\times10^{-6}$ to $10\times10^{-24}$ vol.-%.

This application relates to subject matter disclosed in German Application number 197 42 299.3, filed on Sep. 25, 1997, the disclosure of which is incorporated herein by reference.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A system comprising a device (4) for the amplification of electromagnetic oscillations by means of induced emission through a solid element, crystals or glasses doped with neodymium, semiconductor diodes or liquids or gases; a cable (2) having an outlet opening, said cable being coupled to said device for conducting electromagnetic oscillations emerging from said device to said outlet opening of said cable; a container containing a quantity of a substance composed of a solid element, or a gaseous or liquid; a treatment probe having an inlet opening to which said outlet opening of said cable is coupled, said treatment probe having an outlet opening and defining a path for conducting the electromagnetic oscillations from said inlet opening to said outlet opening of said treatment probe, said treatment probe further having a crosswise opening that is located between said inlet opening and said outlet opening of said treatment probe and extends across the path for receiving said container so that electromagnetic oscillations emerging from the cable (2) are conducted through the substance.

2. System according to claim 1, wherein the treatment probe (3) has a longitudinal opening (9) which extends between said inlet opening and said outlet opening of said treatment probe and which contains said path and wherein said crosswise opening intersects said longitudinal opening (9) at an angle.

3. System according to claim 1, wherein said container (12) is made of glass or quartz glass.

4. System according to claim 1, wherein the container (12) is provided with a closure mechanism (14).

5. System according to claim 1, wherein the device (4) is an argon-ion laser, or an argon-ion multi-line laser for frequencies ranging from $5\times10^{14}$ Hz to $5\times10^{15}$ Hz.

6. System according to claim 1, wherein the substance is a liquid mixture containing a homeopathic substance present in a concentration of 90 vol.-% to $10\times10^{-24}$ vol.-%.

7. System according to claim 1, wherein the device (4) has a power output between 30 mW and 100 mW or 40 mW and 70 mW or 45 mW and 65 mW or 45 mW and 55 mW, especially 50 mW.

8. System according to claim 1, wherein the device (4) is an argon-ion-krypton mixed-gas laser.

9. System according to claim 1, wherein the device (4) is an He—Ne laser, or an He—Cd laser, or a multi-line/single-line laser, or a multi-mode or variable-frequency laser, or a diode laser emitting at a frequency between $5\times10^{14}$ and $10^{15}$ Hz.

10. System according to claim 9, wherein the device (4) is a crystal laser, or a Nd-YAG laser.

11. System according to claim 1, wherein the substance (8) is present in a concentration of $10\times10^{-3}$ vol.-% to $10\times10^{-9}$ vol.-% and is provided for the treatment of contusions.

12. System according to claim 1, wherein the substance (8) is present in a concentration of $10\times10^{-3}$ vol.-% to $10\times10^{-12}$ vol.-% and is provided for the treatment of broken bones, and the device (4) is an argon-ion laser.

13. System according to claim 1, wherein the substance (8) is present in a concentration of $10\times10^{-6}$ vol.-% to $10\times10^{-8}$ vol.-% and is provided for the treatment of tumors, and the device (4) is an argon-krypton mixed-gas laser.

14. System according to claim 1, wherein the substance (8) is present in a concentration of $10\times10^{-3}$ vol.-% to $10\times10^{-9}$ vol.-% and is provided for the treatment of concussions, and the device (4) is an argon-ion laser.

15. System according to claim 1, wherein the substance (8) is present in a concentration of $10\times10^{-1}$ vol.-% to $10\times10^{-24}$ vol.-% and is provided for the treatment of metabolic disorders, and the device (4) is an argon-ion laser, or an argon-krypton mixed-gas laser, or a diode laser, or an Nd-YAG laser, or an He—Ne laser, or an He—Cd laser.

16. System according to claim 1, wherein the substance (8) is present in a concentration of 100 vol.-% to $10\times10^{-24}$ vol.-% and is provided for the treatment of cell cultures, and the device (4) is an argon-ion laser, or an argon-krypton laser, or a krypton laser, or a diode laser, or an Nd-YAG laser, or an He—Ne laser, or an He—Cd laser.

* * * * *